United States Patent [19]

Ward

[11] 4,113,787
[45] Sep. 12, 1978

[54] AROMATIC HYDROCARBON DEHYDROGENATION PROCESS

[75] Inventor: Dennis J. Ward, South Barrington, Ill.

[73] Assignee: UOP Inc., Des Plaines, Ill.

[21] Appl. No.: 758,092

[22] Filed: Jan. 10, 1977

[51] Int. Cl.$^2$ .................. C07C 15/09; C07C 15/10
[52] U.S. Cl. ................................. 260/669 R
[58] Field of Search ..................... 260/669 R

[56] References Cited

U.S. PATENT DOCUMENTS

| | | | |
|---|---|---|---|
| 3,409,689 | 11/1968 | Ward | 260/669 R |
| 3,525,776 | 8/1970 | Berger | 260/669 R |
| 3,702,346 | 11/1972 | Kellar | 260/669 R |
| 3,847,968 | 11/1974 | Hughes | 260/669 R |

*Primary Examiner*—O. R. Vertiz
*Assistant Examiner*—Wayne A. Langel
*Attorney, Agent, or Firm*—James R. Hoatson, Jr.; John F. Spears, Jr.; William H. Page, II

[57] ABSTRACT

Alkylaromatic hydrocarbons including ethylbenzene are dehydrogenated in a vapor phase reactant stream, preferably at subatmospheric conditions. The resultant reaction zone effluent is partially condensed and then separated in a subatmospheric product settler. Hydrocarbons from the product settler are fractionated to yield a styrene bottoms stream, an overhead liquid recycled to the reaction zone and an overhead vapor. This vapor is admixed with vapors from the product settler, compressed to a superatmospheric pressure, and partially condensed to form a liquid which is fractionated to remove the net light aromatic hydrocarbons produced in the process.

7 Claims, 1 Drawing Figure

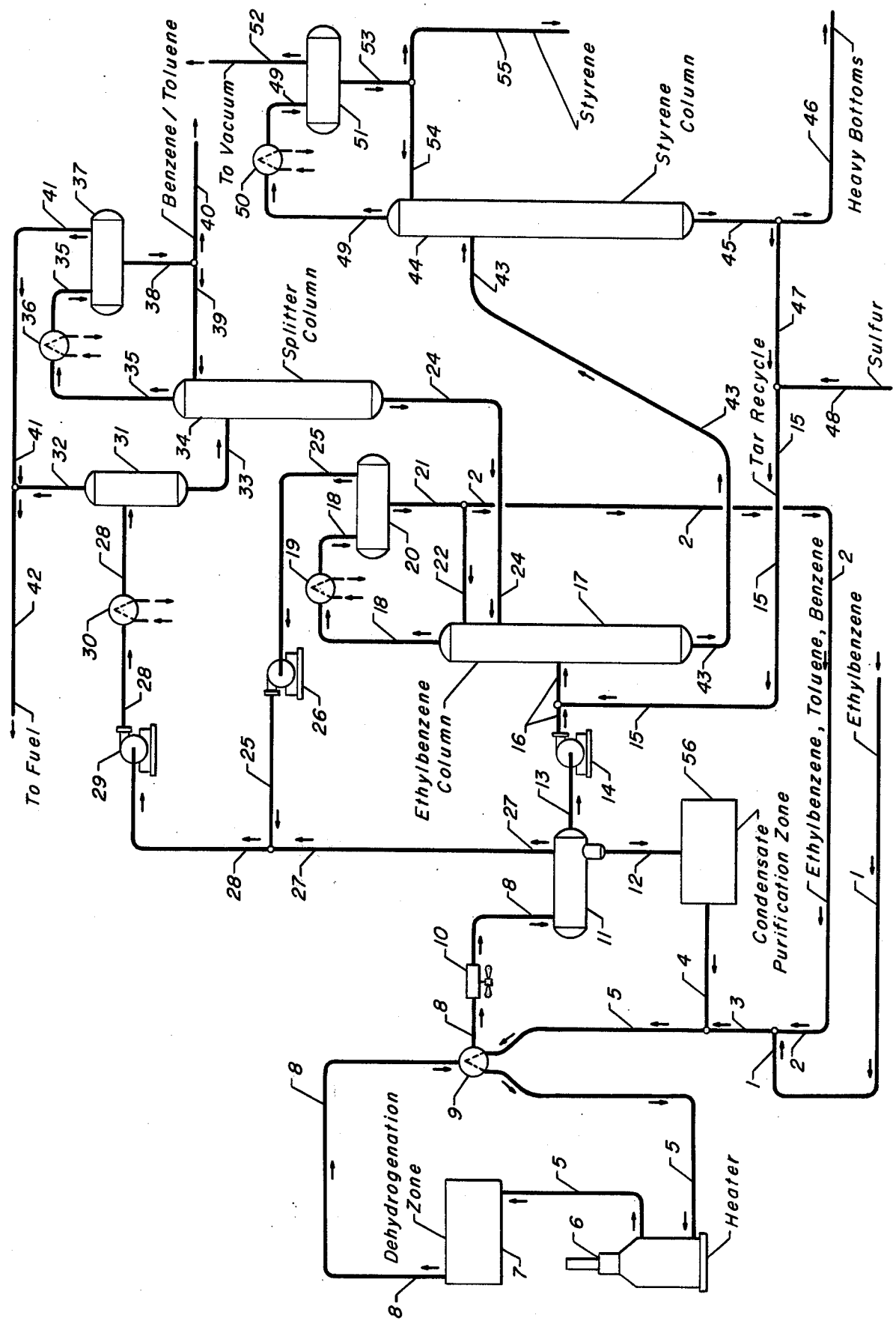

AROMATIC HYDROCARBON DEHYDROGENATION PROCESS

FIELD OF THE INVENTION

The invention relates to the processing of mineral oils. It more specifically relates to a process for the dehydrogenation of aromatic hydrocarbons and for the subsequent fractionation of the materials formed by this dehydrogenation. The invention therefore relates to processes similar in nature to those found in Classes 203-2 and 260-669R.

PRIOR ART

The dehydrogenation of aromatic hydrocarbons is well established in the art. It is performed commercially for the production of styrene from ethylbenzene to fulfill the sizable demand for this polymeric starting material. Styrene may be polymerized with itself or it may be copolymerized with butadiene, isoprene, acrylonitrile, etc. Processes for the dehydrogenation of ethylbenzene are often integrated with an alkylation process for the production of the ethylbenzene as shown in U.S. Pat. No. 3,525,776 (Cl. 260-669).

The vapor phase dehydrogenation of ethylbenzene in a reaction zone maintained at a subatmospheric pressure and the use of superheated steam in the reaction zone is taught by U.S. Pat. No. 3,847,968 (Cl. 260-669R). The steam is used as a diluent to reduce the partial pressure of the styrene and to supply sensible heat consumed by the endothermic dehydrogenation reaction. The subatmospheric distillation of the hydrocarbons in the reaction zone effluent is also taught by this reference. The condensed hydrocarbons from the product settler or phase separation zone are passed into a first fractionation column which removes benzene and toluene as an overhead product. A bottoms stream comprising ethylbenzene and styrene is passed into a second column which removes ethylbenzene as the overhead product. The bottoms stream of the second column is passed into a styrene column which removes high boiling impurities from a styrene product stream taken from the top of the column. Other references showing the subatmospheric styrene fractionation include U.S. Pat. Nos. 3,408,263; 3,408,264 (Cl. 203-2) and 3,408,266 (Cl. 203-9). These three references utilize a single fractionation column into which the hydrocarbon effluent of the reaction zone is passed.

U.S. Pat. No. 3,702,346 (Cl. 260-669R) describes an ethylbenzene dehydrogenation process wherein the product settler in which the condensed reaction zone effluent is separated is maintained at a subatmospheric pressure. An off-gas stream is removed from the settler to maintain the subatmospheric pressure. This stream is described as comprising a small amount of water, hydrogen, methane, ethane, ethylene, carbon monoxide and carbon dioxide.

The recycling of toluene from the product fractionation zone to the dehydrogenation zone is taught in U.S. Pat. No. 3,409,689 (Cl. 260-669) and in British patent specification No. 1,238,602. Various other methods of handling the effluent of the dehydrogenation zone are presented in U.S. Pat. Nos. 3,515,764; 3,515,765; 3,515,766; 3,515,767 and 3,629,076.

DESCRIPTION OF THE DRAWING

The Drawing illustrates the preferred embodiment of the invention. For clarity and simplicity, various subsystems and apparatus normally utilized in the operation of the process have not been shown. These items include flow and pressure control valves, control and monitoring systems, reactor and fractionator internals, reboilers, pumps, etc. These apparatus may be of customary design as they do not form part of the inventive concept. This representation of the preferred embodiment of the invention is not intended to preclude from the scope of the invention those other embodiments set out herein or which are the result of reasonable and normal modification of these embodiments. It is also not intended to limit the preferred embodiment to the use of specific optional or alternative features described herein.

Referring now to the Drawing, a preferably pure ethylbenzene feed stream enters the process through line 1. It is admixed with a recycle stream comprising ethylbenzene, benzene and toluene from line 2 and passed through line 3. At the junction with line 4 the material in line 3 is admixed with a liquid phase condensate stream and passed into line 5. The resultant admixture is vaporized in a heat exchanger 9 and superheated in a fired heater 6. This results in a superheated mixture of steam, ethylbenzene, toluene and benzene which is passed through a dehydrogenation zone 7 under dehydrogenation conditions which in the preferred embodiment include a subatmospheric pressure. The effluent of the dehydrogenation zone is removed in line 8 for cooling in heat exchanger 9 and if desired in a steam generation zone not shown. This effluent stream is then partially condensed in cooler 10, and the resultant mixed phase stream is passed into a phase separation zone shown as being formed by a product settler 11. As used herein the term "reaction zone" is intended to refer to the dehydrogenation zone.

The product settler is maintained at a subatmospheric pressure by the withdrawal in line 27 of a vapor stream which comprises benzene, toluene, styrene and ethylbenzene and reaction by-products including hydrogen, carbon dioxide, ethylene, water vapor and methane. Most of the $C_6+$ hydrocarbons in the dehydrogenation zone effluent are collected as a liquid phase and removed in line 13. This hydrocarbon phase is caused to flow through line 16 by a pump 14 and is admixed with a stream of polymers and sulfur recycled in line 15. This recycling is an optional method of reducing styrene polymerization in the fractionation columns. A liquid water stream is removed from the product settler in line 12 and passed through a condensate purification zone 56. In this zone undesired aromatic hydrocarbons are removed, as by stripping and filtration, to produce the condensate stream of line 4.

Fractionation column 17 is operated at a subatmospheric pressure and other conditions which effect the separation of substantially all entering styrene and $C_9+$ hydrocarbons into a bottoms stream removed in line 43. This bottoms stream is further fractionated in the styrene column 44 to separate out the $C_9+$ hydrocarbons and sulfur into a bottoms stream removed in line 45. A net bottoms stream is removed in line 46, with the remaining portion of this stream passing through line 47. Makeup inhibitor sulfur is added through line 48 to form the inhibitor stream of line 15. An overhead vapor stream is removed in line 49 and fairly completely condensed in overhead condenser 50. The resultant liquid and remaining vapors are collected in an overhead receiver 51. A small vapor stream resulting from air leaks and dissolved gases is removed in line 52 to maintain a low pressure in the column. A liquid stream withdrawn through line 53 is divided into a reflux stream carried by line 54 and a net styrene product stream removed in line 55.

Fractionation column 17 is referred to as the ethylbenzene column because ethylbenzene is removed in the overhead vapors. These vapors are removed in line 18 and partially condensed in overhead condenser 19, with the resultant mixed phase stream being passed into an overhead receiver 20. The liquid phase material is withdrawn in line 21 to form a reflux stream carried by line 22 and a stream of overhead liquid carried by line 2. A vapor stream comprising hydrogen, carbon dioxide, methane, etc., which were dissolved in the liquid removed from the product settler is removed in line 25. This vapor stream also contains the majority of the benzene and toluene present in the dehydrogenation zone effluent and a very small amount of styrene and ethylbenzene. The remaining benzene and toluene in the dehydrogenation zone effluent is found dissolved in the water in line 12 or in the vapor stream of line 27.

The vapor stream in line 25 is increased in pressure in compressor 26 and admixed with the vapor stream from line 27. The resultant combined vapor stream passes through line 28 to a second compressor 29. It is then further pressurized and partially condensed in a cooler 30, with the resultant mixed-phase stream being passed into a vapor-liquid settler 31 which is also referred to herein as a second phase separation zone. The vapor stream removed from this settler in line 32 contains hydrogen, carbon dioxide, methane and ethane. Substantially all $C_6+$ hydrocarbons which were carried by line 28 pass through line 33 to a splitter column 34. This fractionation column is operated under conditions which produce a bottoms stream comprising benzene, toluene, ethylbenzene and styrene. This bottoms stream is removed in line 24 and passed into the ethylbenzene column at an upper intermediate point above line 16.

The splitter column overhead vapor stream is removed in line 35 and passed through an overhead condenser 36. The resultant mixed-phase stream is separated in an overhead receiver 37. The uncondensed hydrogen, carbon dioxide, methane and ethane are removed in line 41. Admixture with the vapor stream from line 32 produces a fuel gas stream removed in line 42. The liquid phase overhead material is removed in line 38. A first portion is returned to the splitter as reflux in line 39. A second portion, which is approximately equal to the net rate of benzene and toluene production in the process, is removed in line 40. This product stream is a substantially pure mixture of benzene and toluene.

DETAILED DESCRIPTION

Present commercial processes for the dehydrogenation of alkylaromatics, such as ethylbenzene, are normally high temperature vapor-phase operations which pass a sizable amount of steam through the reaction zone. They also share the common characteristics of effecting a less than total conversion of the ethylbenzene, operating at a relatively low pressure and requiring the recycle of various streams through the reaction zone. These characteristics make necessary the expenditure of a large amount of energy for vaporization and condensation operations, heating, cooling and compression. The prior art has therefore resorted to known methods of heat exchange, etc. and developed specialized procedures which make the dehydrogenation process more efficient. It is an objective of this invention to provide a process for the dehydrogenation of alkylaromatic hydrocarbons including ethylbenzene. It is a further objective to provide a dehydrogenation process with a more efficient separation of the reaction zone effluent.

A basic element of the present invention is the intentional incomplete condensation of the $C_6$ and $C_7$ hydrocarbons in the dehydrogenation zone effluent stream prior to passage of this stream into the phase separation zone or product settler. A second basic element of the invention is the incomplete condensation of the $C_6$ and $C_7$ hydrocarbons in the overhead vapor stream of the ethylbenzene column into which the liquid hydrocarbons withdrawn from the product settler are passed. Both of these steps are conducted at a subatomospheric pressure to aid in retaining benzene and toluene in the vapor phase during the condensations. The two vapor streams resulting from these two partial condensations are then preferably admixed, pressurized and cooled to effect another condensation which results in the condensation of substantially all $C_6+$ hydrocarbons in this stream. These streams may be individually compressed and cooled, but it is preferred that they are admixed prior to cooling. It is also preferred that at least 95 mol.% of the $C_6+$ hydrocarbons in the precursor vapor streams are condensed in this step.

The total amount of benzene and toluene which is present in the vapor streams removed from the product settler and from the overhead receiver of the ethylbenzene column should be at least equal to the net production of benzene and toluene in the dehydrogenation zone. Preferably, this amount should exceed the net rate of benzene and toluene production by at least 10 to 30 mol.%. This results in the presence of sufficient liquid to perform a fractionation operation in the splitter column into which the condensed benzene and toluene is passed. This splitter functions to separate benzene and the net toluene make from the entering liquid into an overhead liquid stream. The bottoms of the splitter is therefore substantially free of benzene and is rich in toluene. That is, it is comprised of over 50 mol.% toluene.

The term "first phase separation zone" is intended to refer to the product settler and these terms are used interchangeably herein. It is preferably maintained at conditions effective to result in the condensation of over 95 mol% of the water present in the reaction zone effluent while simultaneously producing a vapor stream which contains over 5 mol.% benzene. This vapor stream may contain 10 mol.% or more benzene and about 5 mol.% toluene. These conditions are to include a subatmospheric pressure which is preferably within the range of from 200 to 600 mm. Hg. absolute. A temperature of about 35°–40° C. is preferred, but the temperature may range above and below this depending on the absolute pressure utilized within this zone. However, the temperature should be within the range of about 30° C. to 60° C.

The water in the reaction zone effluent steam which is condensed is collected in the product settler. It is removed by decantation and is preferably recirculated as a condensate stream used to form steam passed into the reaction zone. The condensate stream is normally purified in a manner known in the art prior to its vaporization. A suitable method for this is to strip hydrocarbons from the condensate stream and then filter the condensate stream. This method is described in further detail in U.S. Pat. No. 3,515,766. The aqueous condensate stream removed from the product stream need not be recycled to the reaction zone, and an aqueous stream from an external source may be used to form the steam fed to the reaction zone.

The majority of the benzene and toluene which is fed to the splitter column is present in the vapor stream removed from the overhead receiver of the ethylbenzene column. This vapor stream will contain lesser amounts of ethylbenzene and styrene. The ethylbenzene column is operated at conditions which are effective to produce a bottoms stream which is substantially free of ethylbenzene and all lighter hydrocarbons. That is, the total concentration of ethylbenzene, benzene and toluene should be less than 1 mol.% of this bottoms stream. The ethylbenzene column may be operated at the customary subatmospheric condition known in the art. Preferably, the overhead receiver is maintained at a pressure of about 50 to 500 mm. Hg. absolute. A pressure of about 100 mm. Hg. absolute is preferred. This column is operated at a subatmospheric pressure to allow its operation at lower temperatures which produce a lower rate of styrene polymerization. When referring to the pressure maintained within a fractionation column it is, unless otherwise specified, intended to indicate the pressure as measured at the top of the column. Various inhibitors, such as elemental sulfur or 2,4-dinitrophenol may also be added to reduce polymerization. Sulfur is also introduced into the column by returning a portion of the high molecular weight polymeric material removed as the bottoms stream of the styrene purification column. Further details may be obtained by reference to U.S. Pat. Nos. 3,647,637; 3,476,656; 3,408,263; 3,398,063 and 3,222,263 or the other previously cited references.

The bottoms stream of the ethylbenzene column is preferably passed into a styrene or finishing column in the manner shown in the Drawing. This column is operated at the normal and customary conditions known to those skilled in the art. These conditions also include a subatmospheric pressure. Styrene may also be separated from a mixture of liquid hydrocarbons by the use of liquid extraction as described in U.S. Pat. No. 3,424,807; 3,427,362 and 3,437,704.

The combined vapor stream formed by the admixture of the product settler vapor and the ethylbenzene column overhead vapor is compressed to a superatmospheric pressure. A pressure of about 2 atmospheres absolute is preferred, but pressures up to about 20 atmospheres absolute or higher may be applied. The combined vapor stream is then cooled to effect a condensation, and the resultant vapor and liquid phases are separated. The degree of cooling required will be dependent on the pressure to which the combined vapor stream is compressed. A suitable range of temperatures is from about 0° C. to about 70° C., with a temperature of about 30°–40° C. being preferred. The liquid formed by this condensation is passed into a hydrocarbon separation zone. Preferably, this zone comprises a relatively small splitter column which is sufficient to produce a relatively pure benzene and toluene stream as an overhead liquid. It may be operated at customary conditions for this separation. This separation zone may, in its simplest form, be a single flash vessel. If a flashing operation is performed, it is preferably done in a rectified-flash vessel. Suitable means to limit the loss of benzene in the rejected overhead vapors of this zone, such as refrigerated condensation, should be provided. The function of this zone is to separate the condensed liquid into a product stream containing the net benzene and toluene and a bottoms stream which contains toluene or other recycled alkylaromatic hydrocarbon. Any type of separatory system capable of adequately performing this function at normally acceptable conditions and efficiencies may be utilized. The bottoms stream of this separation zone is passed into the ethylbenzene column at a point above the major feed point (line 16) where the key component liquid composition in the column is similar to the composition of the bottoms stream.

In accordance with this description, the preferred embodiment of the invention may be characterized as a process for the production of styrene by the dehydrogenation of ethylbenzene which comprises the steps of admixing a primary feed stream comprising ethylbenzene with an aqueous stream and a recycle stream comprising ethylbenzene, benzene and toluene to thereby form a combined feed stream; passing the combined feed stream through a dehydrogenation zone as a vapor, the dehydrogenation zone being maintained at dehydrogenation promoting conditions, and effecting the formation of a dehydrogenation zone effluent stream which comprises ethylbenzene, styrene, toluene, benzene and hydrogen; cooling and effecting a partial condensation of the dehydrogenation zone effluent stream, and passing the dehydrogenation zone effluent stream into a first phase separation zone maintained at a subatmospheric pressure; withdrawing a first vapor stream comprising hydrogen, toluene and ethylbenzene from the first phase separation zone; withdrawing a first hydrocarbon liquid stream and a liquid water stream from the first phase separation zone; passing the first hydrocarbon liquid stream into an intermediate point of a first fractionation column operated at conditions effective to separate the first hydrocarbon liquid stream into a first overhead vapor stream and a first bottoms liquid stream comprising styrene; passing the first bottoms stream into a second fractionation column operated at conditions effective to produce an overhead product stream of substantially pure styrene; cooling and partially condensing the first overhead vapor stream to effect the formation of a second vapor stream comprising hydrogen, benzene and toluene and a hydrocarbon liquid phase, and removing the hydrocarbon liquid phase as a second hydrocarbon liquid stream comprising benzene, toluene and ethylbenzene, and admixing a portion of the second hydrocarbon liquid stream with the primary feed stream as the aforementioned recycle stream; admixing and effecting a partial condensation of the first vapor stream and the second vapor stream to form a mixed-phase stream which is passed into a second phase separation zone; withdrawing a third vapor stream comprising hydrogen and a third hydrocarbon liquid stream comprising benzene, toluene and ethylbenzene from the second phase separation zone; passing the third hydrocarbon liquid stream into a third fractionation column operated at conditions effective to produce a net overhead liquid stream comprising benzene and toluene and a second bottoms stream comprising toluene and ethylbenzene; and, passing the second bottoms stream into the first fractionation column at an intermediate point above the intermediate point at which the first hydrocarbon liquid stream enters the fractionation column.

The present invention may be applied to any process for the dehydrogenation of alkylaromatic hydrocarbons wherein the dehydrogenation zone effluent is at least partially condensed. The specific mode of operation of the reaction zone or the composition of the catalytic material is not determinative of the usefulness of the invention. The description herein which refers specifically to the dehydrogenation of ethylbenzene is therefore not intended to so limit the invention, as this process may be applied to the dehydrogenation of other alkylaromatic hydrocarbons such as diethylbenzene, ethyltoluene, propylbenzene and isopropylbenzene and also to alkylaromatic hydrocarbons having other ring structures, including naphthalenes and anthracene compounds.

The reaction zone preferably comprises two or three beds of dehydrogenation catalyst with means for the intermediate addition and admixture of steam. Suitable systems are presented in U.S. Pat. Nos. 3,498,755; 3,515,763; and 3,751,232. The catalyst beds may be contained in separate reaction vessels and may have either a cylindrical or an annular shape. Different catalysts may be used in different beds as described in U.S. Pat. No. 3,223,743. Such catalysts generally consist of one or more metallic components selected from Groups VI and VIII of the periodic table. These metallic components are typically carried on a refractory inorganic oxide material such as alumina, silica, boria or mixtures thereof. One typical catalyst comprises 85% by weight ferric oxide, 2% chromia, 12% potassium hydroxide and 1% sodium hydroxide. A second typical catalyst comprises 90% by weight iron oxide, 4% chromia and 6% potassium carbonate. Methods for preparing suitable catalysts are well known in the art. This is demonstrated by the teachings of U.S. Pat. No. 3,387,053, which describes the manufacture of a catalytic composite of at least 35 wt.% iron oxide as an active catalytic agent, from about 1 to 8 wt.% zinc or copper oxide, about 0.5 to 50 wt.% of an alkali promoter, and from about 1 to 5 wt.% chromic oxide as a stabilizer and a binding agent. Catalysts preferably employed are available commercially and are commonly referred to as "Shell 105" or "Shell 205".

Dehydrogenation conditions in general include a temperature of about 1000° F. to about 1800° F. and preferably about 1050° F. to about 1250° F. The temperature required for any specific unit will depend on the activity of the catalyst employed. The pressure maintained within the dehydrogenation zone is generally quite low and may range from subatmospheric to about 5 atmospheres or higher, with a preferred pressure range being from about 200 to 800 mm. Hg. measured at the reaction zone outlet. The feed stream is charged to the dehydrogenation zone at a liquid hourly space velocity, based on liquid hydrocarbon charge at 60° F., of about 0.1 hr.$^{-1}$ to about 1.0 hr.$^{-1}$, and preferably from 0.2 to 0.7 hr.$^{-1}$.

As previously mentioned, the alkylaromatic to be dehydrogenated is admixed with superheated steam to counteract the temperature lowering effect of the endothermic dehydrogenation reaction. Preferably, the steam is admixed with the feed stream and also added at intermediate points within the reaction zone. As an alternative to using steam, some processes utilize indirect heat exchange of the reactants or heating elements within the catalyst bed. The steam and alkylaromatic hydrocarbon can be separately heated and then mixed prior to contacting the reactants with the catalyst, or the steam and alkylaromatic can be first commingled and then heated. When ethylbenzene is being dehydrogenated, the space velocity, the rate of steam admixture and the inlet temperature are preferably adjusted to result in the effluent of each catalyst bed having a temperature of about 1100° F. Preferably, steam is admixed with the feed stream to the dehydrogenation zone at a rate of about 0.65 to about 1.0 pounds of steam per pound of ethylbenzene. A second portion is added to the effluent of the first catalyst bed at a rate of about 1.0 to about 1.2 pounds of steam per pound of effluent, and a third portion is added to the effluent of the second bed at a rate of about 0.8 to about 1.3 pounds per pound of effluent. These rates are adjusted such that the total effluent stream from the dehydrogenation zone will contain from about 3 to about 6 pounds of steam per pound of styrene. Further details may be obtained by reference to U.S. Pat. Nos. 3,179,706 and 3,387,053.

The effluent stream removed from the dehydrogenation zone is often first heat exchanged for the dual purposes of lowering its temperature in order to prevent polymerization of the styrene and for the recovery of heat. The effluent stream may be heat exchanged against a makeup stream of steam, a reactant stream of this or another process or it may be used as a heat source for fractional. Commercially, the effluent stream is often passed through several heat exchangers for the heating of different streams. The reaction zone effluent may also be passed through a quench zone to rapidly cool it and lessen polymerization. The quench zone may be located after a heat exchange means as shown in U.S. Pat. Nos. 3,515,765 and 3,515,766, or the effluent stream may pass directly from the reactor into the quench zone as shown in U.S. Pat. No. 3,515,764. The cooling media fed to the quench zone is preferably liquid water removed from the first phase separation zone. The temperature of the effluent stream is finally lowered to within the range set out above by additional cooling.

As used herein the term "alkylaromatic hydrocarbon" is intended to refer to an aromatic hydrocarbon having saturated aliphatic substituents, such as xylenes, ethylbenzene and isopropylbenzene. Likewise, the term "vinyl aromatic hydrocarbon" is intended to refer to an aromatic hydrocarbon having an unsaturated aliphatic substitutent. Examples of this class of compounds include styrene, alpha-methylstyrene, beta-methylstyrene and vinyl toluene.

It is a basic step in the subject process to recirculate an alkylaromatic hydrocarbon other than that forming the main feed stream. This second alkylaromatic hydrocarbon is to contain at least one less carbon atom per molecule than feed alkylaromatic hydrocarbon. It is preferably a methyl-substituted aromatic hydrocarbon, and most preferably is toluene when ethylbenzene is the first alkylaromatic hydrocarbon of the feed stream. The subject process provides a facile method of performing this step. A sufficient amount of toluene and benzene is obtained in the net overhead liquid of the ethylbenzene column. This stream also contains the unconverted ethylbenzene which is recycled to the dehydrogenation zone. Details as to the recycling of this material may be obtained from U.S. Pat. No. 3,409,689 and British patent specification No. 1,238,602. The advantages of recycling toluene include a more selective process and lower utilities costs. The mole ratio of ethylbenzene to toluene is combined reactant stream may vary from about 0.5:1 to 10.0:1. It is also beneficial to recirculate benzene in the same manner as toluene, but toluene is preferred over benzene for recycling in this manner. In the preferred embodiment of the invention both of these hydrocarbons are recycled to the dehydrogenation zone.

I claim as my invention:

1. A process for the production of styrene by the dehydrogenation of ethylbenzene which comprises the steps of:
   (a) admixing a primary feed stream comprising ethylbenzene with an aqueous stream and a recycle stream comprising ethylbenzene, benzene and toluene to thereby form a combined feed stream;
   (b) passing the combined feed stream through a dehydrogenation zone as a vapor, the dehydrogenation zone being maintained at dehydrogenation promoting conditions, and effecting the formation of a dehydrogenation zone effluent stream which comprises ethylbenzene, styrene, toluene, benzene and hydrogen;
   (c) cooling and effecting a partial condensation of the dehydrogenation zone effluent stream, and passing the dehydrogenation zone effluent stream into a first phase separation zone maintained at a subatmospheric pressure;
   (d) withdrawing a first vapor stream comprising hydrogen, toluene and ethylbenzene from the first phase separation zone;
   (e) withdrawing a first hydrocarbon liquid stream and a liquid water stream from the first phase separation zone;
   (f) passing the first hydrocarbon liquid stream into an intermediate point of a first fractionation column operated at conditions effective to separate the first hydrocarbon liquid stream into a first overhead vapor stream and a first bottoms liquid stream comprising styrene;
   (g) passing the first bottoms stream into a second fractionation column operated at conditions effective to produce an overhead product stream of substantially pure styrene and recovering the latter;
   (h) cooling and partially condensing the first overhead vapor stream to effect the formation of a second vapor stream comprising hydrogen, benzene and toluene and a hydrocarbon liquid phase, and removing the hydrocarbon liquid phase as a second hydrocarbon liquid stream comprising benzene, toluene and ethylbenzene, and admixing a portion of the second hydrocarbon liquid stream with the primary feed stream as the aforementioned recycle stream;
   (i) admixing and effecting a partial condensation of the first vpaor stream and the second vapor stream to form a mixed-phase stream which is passed into a second phase separation zone;
   (j) withdrawing a third vapor stream comprising hydrogen and a third hydrocarbon liquid stream comprising benzene, toluene and ethylbenzene from the second phase separation zone;
   (k) passing the third hydrocarbon liquid stream into a third fractionation column operated at conditions effective to produce a net overhead liquid stream comprising benzene and toluene and a second bottoms stream comprising toluene and ethylbenzene; and,
   (1) passing the second bottoms stream into the first fractionation column at an intermediate point above the intermediate point at which the first hydrocarbon liquid stream enters the first fractionation column.

2. The process of claim 1 further limited in that the liquid water stream of step (e) is passed through a purification zone wherein aromatic hydrocarbons are removed to form the aqueous stream of step (a).

3. The process of claim 1 further limited in that after being partially condensed, the first overhead vapor stream is passed into an overhead receiver maintained at a subatmospheric pressure.

4. The process of claim 3 further limited in that the second phase separation zone is maintained at a superatmospheric pressure.

5. The process of claim 4 further limited in that the dehydrogentation conditions maintained in the dehydrogenation zone include a subatmospheric pressure.

6. A process for the dehydrogenation of an alkylaromatic hydrocarbon which comprises the steps of:
   (a) admixing a primary feed stream comprising a first alkylaromatic hydrocarbon with an aqueous stream and a recycle stream comprising a second alkylaromatic hydrocarbon to thereby form a combined feed stream;
   (b) passing the combined feed stream through a dehydrogenation zone as a vapor, the dehydrogenation zone being maintained at dehydrogenation promoting conditions, and effecting the formation of a dehydrogenation zone effluent stream which comprises benzene, a vinyl aromatic hydrocarbon, the first and the second alkylaromatic hydrocarbons, and hydrogen;
   (c) cooling and effecting a partial condensation of the dehydrogenation zone effluent stream, and passing the dehydrogenation zone effluent stream into a first phase separation zone maintained at a subatmospheric pressure;
   (d) withdrawing a first vapor stream comprising hydrogen, benzene and the second alkylaromatic hydrocarbon from the first phase separation zone;
   (e) withdrawing a first hydrocarbon liquid stream and a liquid water stream from the first phase separation zone;
   (f) passing the first hydrocarbon liquid stream into an intermediate point of a first fractionation column operated at conditions effective to separate the first hydrocarbon liquid stream into a first overhead vapor stream and a first bottoms liquid stream comprising the vinyl aromatic hydrocarbon;
   (g) cooling and partially condensing the first overhead vapor stream to effect the formation of a second vapor stream comprising hydrogen, benzene and the second alkylaromatic hydrocarbon and a hydrocarbon liquid phase, and removing the hydrocarbon liquid phase as a second hydrocarbon liquid stream comprising the first alkylaromatic hydrocarbon and the second alkylaromatic hydrocarbon, and admixing a portion of the second hydrocarbon stream with the primary feed stream as the aforementioned recycle stream;
   (h) admixing and effecting a partial condensation of the first vapor stream and the second vapor stream to form a mixed-phase stream which is passed into a second phase separation zone;
   (i) withdrawing a third vapor stream comprising hydrogen and a third hydrocarbon liquid stream comprising benzene and the first and the second alkylaromatic hydrocarbons from the second phase separation zone;
   (j) passing the third hydrocarbon liquid stream into a hydrocarbon separation zone operated at conditions effective to produce a first hydrocarbon separation zone effluent stream comprising benzene and the second alkylaromatic hydrocarbon and a second hydrocarbon separation zone effluent stream comprising the first and the second alkylaromatic hydrocarbons;

(k) passing the second hydrocarbon separation zone effluent stream into the first fractionation column at an intermediate point above the intermediate point at which the first hydrocarbon liquid stream enters the first fractionation column; and, (l) recovering the vinyl aromatic hydrocarbon from the first bottoms liquid stream.

7. The process of claim 6 further limited in that the second alkylaromatic hydrocarbon is toluene and the first alkylaromatic hydrocarbon is ethylbenzene.

* * * * *